(12) United States Patent
Takahashi et al.

(10) Patent No.: US 6,290,907 B1
(45) Date of Patent: *Sep. 18, 2001

(54) SAMPLE HANDLING SYSTEM

(75) Inventors: Katsushi Takahashi; Mikio Komata; Toshiyuki Ikeda, all of Hitachinaka (JP)

(73) Assignee: Hitachi, Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/150,931

(22) Filed: Sep. 10, 1998

(30) Foreign Application Priority Data

Sep. 11, 1997 (JP) .................................................... 9-246649

(51) Int. Cl.[7] ........................... G01N 35/02; G01N 35/04
(52) U.S. Cl. ................................ 422/65; 422/63; 422/64; 422/67; 422/100; 436/47; 436/48; 436/50; 436/18; 700/266; 700/226
(58) Field of Search .................................. 422/65, 63, 67, 422/100, 103; 436/43, 47, 48; 700/266, 226

(56) References Cited

U.S. PATENT DOCUMENTS

| 4,692,308 | * | 9/1987 | Riley et al. ............................. | 422/65 |
|---|---|---|---|---|
| 5,087,423 | | 2/1992 | Ishibashi . | |
| 5,207,986 | * | 5/1993 | Kadota et al. ......................... | 422/65 |
| 5,209,903 | * | 5/1993 | Kanamori et al. ..................... | 422/65 |
| 5,232,081 | * | 8/1993 | Kanamori ........................... | 198/465.2 |
| 5,350,564 | * | 9/1994 | Mazza et al. .......................... | 422/63 |
| 5,366,062 | * | 11/1994 | Markin et al. ....................... | 198/345.3 |
| 5,380,488 | * | 1/1995 | Wakatake ............................... | 422/65 |
| 5,623,415 | * | 4/1997 | O'Bryan et al. ................. | 364/478.13 |
| 5,876,670 | * | 3/1999 | Mitsumaki et al. .................... | 422/65 |
| 5,902,549 | * | 5/1999 | Mimura et al. ........................ | 422/65 |
| 6,019,945 | * | 2/2000 | Ohishi et al. .......................... | 422/65 |
| 6,141,602 | * | 10/2000 | Igarashi et al. ...................... | 700/226 |

FOREIGN PATENT DOCUMENTS

| 629858 A1 | * | 10/1993 | (EP) . |
|---|---|---|---|
| 63-271164 | * | 11/1988 | (JP) . |
| 3-183957 | * | 8/1991 | (JP) . |

OTHER PUBLICATIONS

Hitachi Review, vol. 41, No. 4, 1992, "Total Clinical Laboratory Testing System for Laboratory Automation", T. Ikeda et al, pp. 167–172.

* cited by examiner

Primary Examiner—Jill Warden
Assistant Examiner—Kathryn Bex
(74) Attorney, Agent, or Firm—Mattingly, Stanger & Malur, P.C.

(57) ABSTRACT

A sample handling system comprising: a transportation line including a combination of plural partitive line units; and a plurality of handling units, wherein each of the plural partitive line units and each of the plurality of handling units form a pair, and each handling unit is installed removably from its corresponding partitive line unit. Each handling unit transmits inoperative information to the transportation line when it becomes inoperative. The transportation line transmits this inoperative information to the central controller. The central controller monitors handling units at which the sample rack can stop over. The sample rack avoids stopover at the inoperative handling unit, but is allowed to advance to the subsequent handling unit passing through the partitive line unit which makes a pair with the inoperative handling unit.

9 Claims, 6 Drawing Sheets

SAMPLE HANDLING SYSTEM

BACKGROUND OF THE INVENTION

The present invention relates to a sample handling system, and in particular, it relates to a sample handling system suitable for automatically carrying out sample testing in clinic laboratories.

A normal sample handling system is comprised of various types of handling units such as a centrifuge, cap-opener, aliquoter, bar code labeler, cap restoppler, sorter, analyzer units, a built-in rack conveyer provided in each handling unit, and a transportation line which connects these handling units, with series connection between a handling unit and another handling unit, between the transportation line and the handling unit, or between a transportation line and another transportation line.

"Hitachi Review, vol.41, No.4, pp.167–172 (1992)" discloses an automatic sample handling system in which the transportation line for transporting samples is comprised of plural transportation routes whereby the transportation line can be diverged into plural branch lines thereby allowing the samples to be distributed to various handling units.

Sample handling units disposed within this system include: an automated centrifuge unit which separates blood sample into serum and cells; a cap opener unit which automatically removes caps from sample containers; an aliquoter unit which aliquotes serum from mother sample containers to daughter sample containers; a bar code labeler unit which labels a bar code label having the same sample ID as the mother sample on the daughter sample container; a restopper unit which restops the sample containers with a cap; a sample sorting unit which sorts out the sample containers into groups of testing; a chemical analyzer unit which automatically analyzes samples chemically, and so on.

Another prior art analyzer system is also known which is provided with a plurality of analyzing modules and has an arrangement to allow samples to stop over at the plurality of analyzing modules by transporting the samples by its transportation line.

U.S. Pat. No. 5,087,423 discloses an arrangement wherein a plurality of analyzing routes are provided corresponding to a plurality of analyzing modules respectively, and a bypass route is provided for sample containers to bypass some of the plurality of analyzing routes. In this example, while a certain sample container which contains a sample to be analyzed is selectively guided to a proper analyzing route, a sample container which contains another sample which does not need to be analyzed is selectively guided to the bypass route. Thereby, each sample is ensured to call only at a proper analyzing module whereby each sample needs to be analyzed.

Further, U.S. Pat. No. 5,380,488 discloses an arrangement in which a sampling feeder having a sampling line and a rack recovery line is disposed corresponding to each analyzer, and a coupling feeder is disposed between respective sampling feeders. Then, a unit combination which is formed by combining the sampling feeder, the coupling feeder and each analyzer is connected with each other to form a plurality of such combination thereby enabling to increase the capability of its analyzing functions.

According to the above-mentioned U.S. Pat. No. 5,087,423, a sample which does not need analysis by a particular analyzing module in the system is caused to stop over at another analyzing module by detouring past the particular analyzing module. However, U.S. Pat. No. 5,087,423 does not teach nor suggest how to operate the system in case of a failure of a part of the plurality of analyzing modules within the system, or in the case of maintenance work being necessitated on a part of the plurality of analyzing modules.

Further, U.S. Pat. No. 5,380,188 which discloses a large scaled system which is facilitated by integrating plural combination units each including a sampling feeder, coupling feeder and analyzer, however, the patent does not teach nor suggest how to operate the system in case of a failure or stoppage of a part of the plural analyzers in the system, or in the case of maintenance of the system.

SUMMARY OF THE INVENTION

An object of the invention is to provide a sample handling system which, even if a part of plural sample handling units within the system fails or becomes inoperative to treat a sample, allows sample handling to be continued by the other sample handling units.

Another object of the invention is to provide a sample handling system which, in case one of plural handling units which is assigned to carry out a particular treatment on a sample held in a sample rack becomes inoperative or under maintenance work, can proceed to forward the sample rack to a subsequent handling process by detouring the failed sampling unit.

The sample handling system according to the invention is constructed by combining a plurality of sample handling units for treating samples held in a sample rack transported by a sample transportation line, and by disposing the plurality of sample handling units along the sample transportation line, further the same is characterized by comprising: a means for reading identification (ID) information of the sample rack and each sample; and a central controller for controlling the sample transportation line, wherein the central controller: monitors operating status of the plurality of handling units; determines, on the basis of information on the status monitored and of ID information having been read, whether or not to allow the sample rack to stop over at any of the plurality of handling units; providing information having been determined on a destination to the sample transportation line; and whereby the sample transportation line controls transportation of the sample rack in response to the destination information having been provided.

In the sample handling system according to the invention, sample transportation line is arranged to include each transportation line unit which is provided as a pair for each one of the plural handling units, and wherein each one of the plural handling units is set up to be removable from its paired each transportation line unit.

The sample handling system of the invention is provided with: the transportation line for transporting the sample rack which holds samples; a rack loading device for supplying the sample rack to the transportation line; a rack storage device for storing the sample rack transported by the transportation line; and the plurality of handling units for applying physical treatment to the samples held in the sample rack, or performing some action on sample containers containing the samples. The plurality of handling units are arranged along the transportation line.

The sample handling system of the invention which is provided with an ID information reader to read out ID information on the sample rack to be transported, monitors operational status of each handling unit, and is provided with the central controller which determines for a specific sample rack which handling unit to stop over at on the basis of the monitoring and the ID information thereof having been read.

Each handling unit transmits inoperative information to the transportation line when its handling unit is in an inoperative state. The transportation line in response to this inoperative information from the inoperative handling unit transmits this inoperative information to the central controller. Then, the central controller controls the transportation of the sample rack to advance on the transportation line without stopping at the inoperative handling unit.

The transportation line of the invention is comprised of a plurality of partitive line units connected in series, provided in pair with the plural handling units. After any one of the plural handling units has been removed from its partitive line unit coupled therewith, the sample rack is still allowed to advance on the partitive line unit from which the handling unit has been removed. The sample rack designated to drop in at a particular handling unit among the plural handling units is allowed to be delivered through its partitive line unit into the particular handling unit only when there exists no preceding sample rack on the partitive line unit provided in pair with the particular handling unit.

A rack withdrawing area is provided for withdrawing a sample rack in the vicinity of the read-out position by the ID information reader. In case any sample rack fails to be read out by the ID information reader, it is withdrawn into the rack withdrawing area without allowing it to advance to any handling unit.

DESCRIPTION OF THE PREFERRED EMBODIMENT

Figure 1:
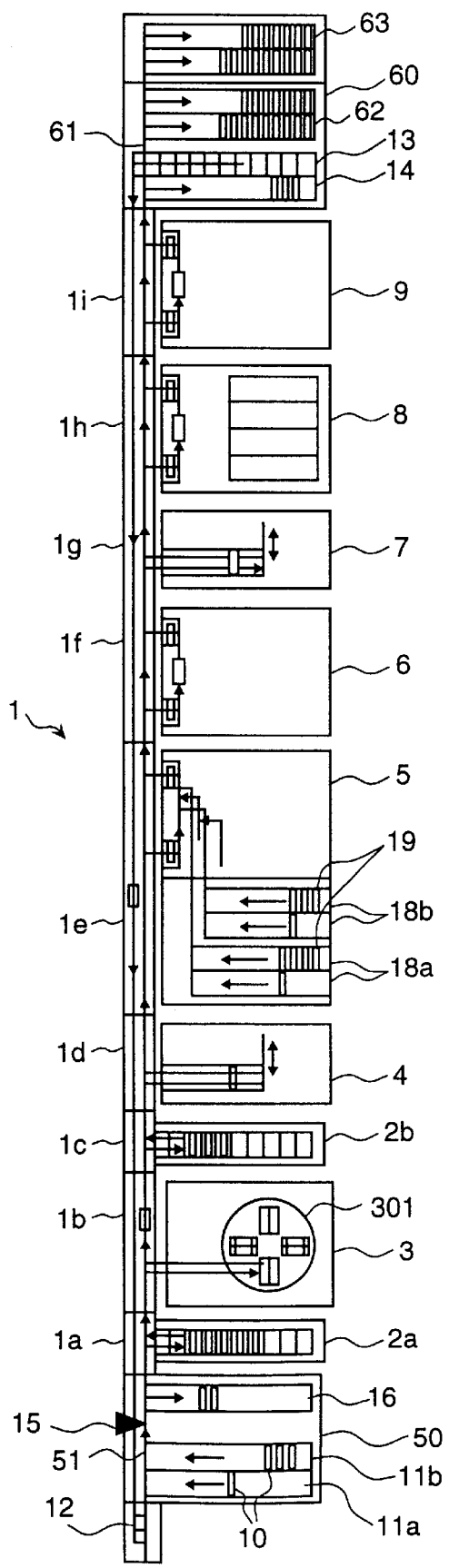
FIG. 1 is a schematic block diagram indicating a sample handling system of one embodiment of the invention, and an arrangement of a plurality of handling units therefor.
Figure 2:
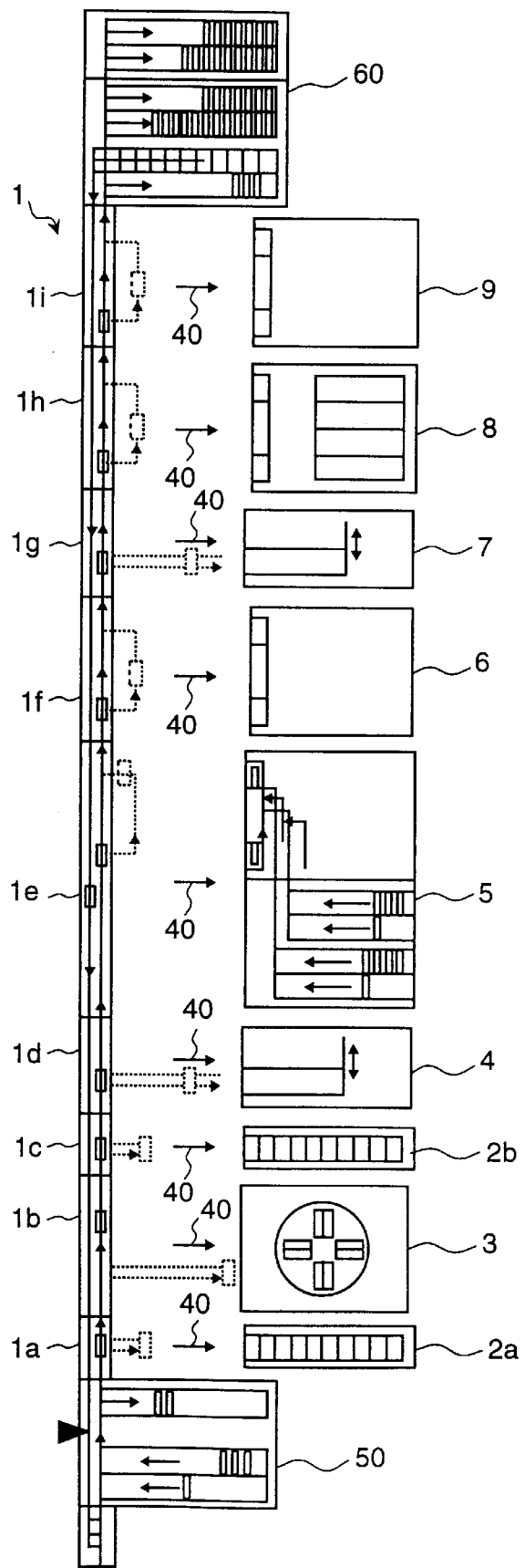
FIG. 2 is a schematic block diagram indicating the sample handling system of FIG. 1, in which the whole of the plurality of handling units are depicted to have been separated from the transportation line.

FIG. 1 is a schematic block diagram indicating the main part of a sample handling system according to one embodiment of the invention. FIG. 2 is a schematic block diagram indicating a status of FIG. 1 in which the whole portions of its handling units are removed from its transportation line.

With reference to FIGS. 1 and 2, a transportation line 1 is disposed between a rack loading device 50 and a rack storage device 60. Rack loading device 50 is provided with: rack mounting areas 11a and 11b capable of directly mounting a rack tray for carrying sample racks; a code reader line 51 for moving a sample rack 10 pushed out from the rack mounting areas one by one to a position at which ID information thereof is read; a bar code reader 15 which serves as an ID information reader; and a rack withdrawing area disposed in the vicinity of the code reader position and in the direction of downstream of the rack movement.

Rack storage device 60 is provided with: a terminal line 61 for withdrawing sample racks 10 having been transported via transportation line 1; a default buffer area 14 for withdrawing, via terminal line 61, sample racks 10, 19 for which normal handling by any one of plural handling units 3–9 was incomplete or failed; a priority sample mounting area 13 which accepts the sample racks withdrawn into the default buffer area for supplying them to a feedback line in the transportation line 1; and a rack storage area 62, 63 for withdrawing and storing sample racks having been successful and completed the transportation work by the transportation line 1.

The transportation line 1 transports the sample rack which holds samples so as to ensure that it will be able to stop over at its designated handling unit. The sample rack which is a holder capable of holding one or more sample containers each containing a sample such as blood, serum or urine, functions as a carrier movable on the transportation line. The transportation line 1 includes a main transportation line for transporting sample racks from the rack loading device 50 to the rack storage device 60, and a feedback transportation line for transporting sample racks in the reverse direction from the rack storage device to the rack loading device when required. This transportation line 1 is comprised of a plurality of partitive line units 1a–1i connected in series, each of which is provided to form a pair with each one of the plurality of handling units 3–9 and buffer units 2a, 2b. Therefore, respective partitive line units serve in part in the main transportation line and the feedback transportation line. Each partitive line unit 1a–1i is provided with a built-in unit controller for controlling the operation in its own unit, and which has a function to communicate with the rack loading device 50 and with the handling unit associated as a pair with its own unit.

Buffer unit 2a withdraws sample racks designated to move to centrifuge unit 3 from transportation line 1 for temporarily retaining them in queue, then returns the sample racks to transportation line 1 when ready to send them to the centrifuge unit 3. Buffer unit 2b withdraws sample racks designated to move to a cap opener unit 4 from transportation line 1 for temporarily retaining them in queue, then returns the sample racks to transportation line 1 when ready to send them to the cap opener unit 4.

The centrifuge unit 3 is a device for separating the whole blood supplied as mother samples to serum and blood-clot. The sample rack holding the mother samples is automatically set on a centrifuge rotor. The cap opener 4 is a device for automatically removing caps from sample containers on the sample rack when they are supplied as capped.

An on-line aliquoter unit 5 is an aliquot device for an on-line analyzer. This aliquoter unit 5 is provided with daughter sample rack loading area 18a, 18b for allowing a plurality of daughter sample racks 19 each holding unused vacant containers to be set therein. When the daughter sample rack 19 is supplied to a pipetting station, the serum is pipetted from the sample containers on the mother sample rack 10 which has moved to the aliquoter unit 5 into a plurality of containers on the daughter sample rack 19. The mother sample rack 10 and the daughter sample rack 19 having been subjected to the pipetting operation are sent to the transportation line 1.

Bar code labeler unit 6 is a device for labeling bar code labels on the sample containers which contain daughter samples. For each daughter sample container, a label having the sample ID as that of the mother sample corresponding thereto is issued. Restopper unit 7 is a device for automatically sealing with caps the sample containers which do not require on-line analysis or off-line pipetting. Sample sorting unit 8 is a device for transferring the containers on sample rack 10, 19 to a plurality of different racks according to different test purposes using a robot hand.

Analyzing unit 9 admits sample rack 10, 19 having containers with their caps removed thereinto, and guides the same to its pipetting station, wherein its pipetting device aspirates a portion of the samples in the sample containers and injects the aspirated sample into reaction vessels. The samples introduced into the reaction vessels are mixed with a reagent, and its reaction solution is measured using a photometer thereby obtaining respective measurement data corresponding to respective analysis items. In place of analyzing unit 9, an off-line aliquoter unit may be used.

Each of buffer units 2a, 2b and handling units 3–9 is provided with a built-in unit controller which controls the operation of its own unit, and has a function to transmit information on the operation of its own unit to its corresponding partitive line unit 1a–1i which is provided in a pair therewith. Of the plurality of handling units 3–9 which are arranged along the transportation line 1, the centrifuge unit 3, aliquoter unit 5 and analyzing unit 9 are such ones which apply physical treatment to the samples held in the sample rack. The analyzing unit 9 applies chemical treatment also to the samples collected in addition to the physical treatment. Further, cap-opener unit 4, bar code labeler unit 6, restoppler unit 7 and sample sorting unit 8 are units that apply some type of operation to the containers containing the samples. Hereinafter, these operations applied to the samples are referred to as the sample handling.

Now, the sample handling operations in the sample handling system of FIG. 1 will be described in detail.

In the case where the samples held in sample racks 10 are normal samples which do not need emergent analysis, the operator of the system inserts these sample racks sequentially into rack mounting areas 11a, 11b in rack loading device 50. In the case where the samples held in sample racks 10 are emergent samples which need emergent analysis, the operator sets these emergent samples at an emergent sample mounting position 12 communicative with the code reader line 51 in the rack loading device 50. When the handling operation starts, the sample racks placed at the emergent sample mounting position 12 are guided to the code reader line 51 with priority to the normal sample racks placed in the normal sample mounting areas 11a, 11b to be transported with priority.

Figure 3:
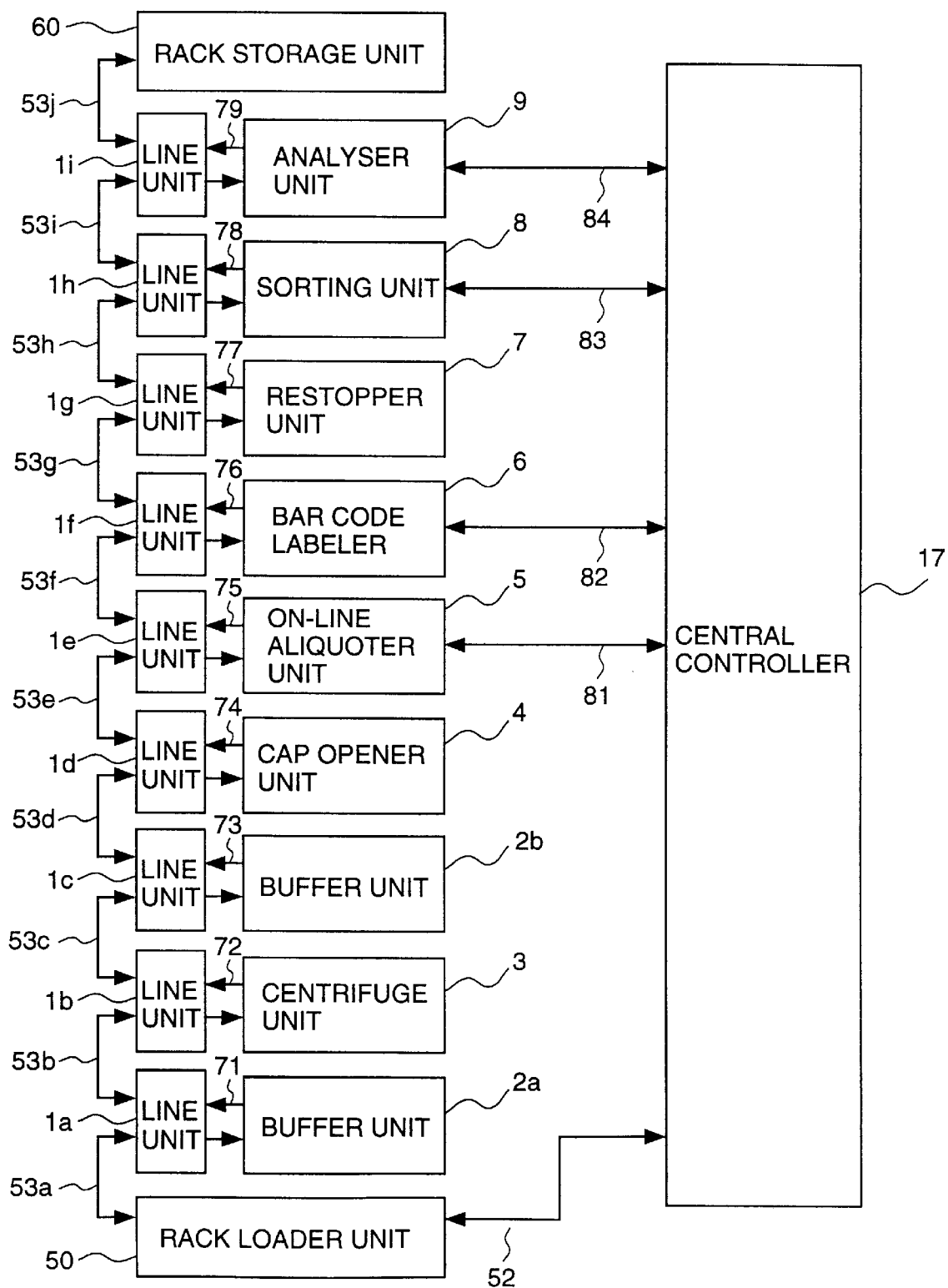
FIG. 3 is a schematic block diagram indicating a mode of communication of information between each one of the plural handling units and the central controller in the sample handling system of the invention.

When sample rack 10 is moved to the read-out position of the reader 15, rack discrimination information (rack ID information) and sample ID information (sample serial no. and sample ID) are read out, and their information displayed in bar codes are transmitted for registration to the central controller 17 which controls the transportation line 1 (refer to FIG. 3). In case the ID information reader 15 fails to read out the rack ID information or the sample ID information, the central controller 17 issues a read error information. Then, on the basis of this read error information, the sample rack the ID information of which was failed to be read out is immediately withdrawn into rack withdrawing area 16 in the rack loading device 50. In this case, the sample rack to be withdrawn is promptly withdrawn into rack withdrawing area 16 without being allowed to move to any handling unit. Because the sample rack the ID information of which failed to be read out is withdrawn into the rack withdrawing area 16 which is disposed in the vicinity of the rack mounting area 11a, 11b, the operator can set this sample rack again in the rack mounting area 11a, 11b. That is, this sample rack is restricted to be transported any further. A sample rack the read-out of the rack ID information and sample ID information of which was successful is allowed to move from the code reading line 51 to partitive line unit 1a adjacent thereto.

Some of the sample racks successfully read out of their rack ID information and sample ID information, and which are designated to move to the centrifuge unit 3 are withdrawn into buffer unit 2a. The number of sample racks acceptable in the buffer unit 2a is limited to the number of sample racks allowed to be mounted on a centrifuge rotor, for example, eight, or until it reaches a predetermined time-out period. When the number of sample racks withdrawn via partitive line unit 1a into the buffer unit 2a reaches the limit condition, the partitive line unit 1a controls such that the buffer unit 2a no more accepts sample racks destined to centrifuge unit 3.

Nextly, under such a condition that no sample rack exists on both partitive line units 1a and 1b, the sample rack which is discharged one by one from buffer unit 2a to partitive line unit 1a is further moved to the adjoining partitive line unit 1b, then is stopped once at a position of entry to centrifuge unit 3. Delivery of the sample rack from this entry position to its mounting position on centrifuge rotor 301 is carried out using a conventional robot hand. The centrifuge rotor 301 applies centrifuge separation to plural sample racks mounted thereon for a predetermined period of time. The sample racks having been subjected to the operation of centrifuge separation are withdrawn one by one to partitive line unit 1b using the robot hand.

A sample rack which does not need a centrifuge separation by centrifuge unit 3 is caused to advance from code reading line 51 to partitive line unit 1c through partitive line units 1a and 1b without stopping thereon.

By provision of the buffer unit 2a in front of centrifuge unit 3, subsequent sample racks subject to centrifuge separation can be kept waiting therein until the preceding sample racks complete their centrifuge separation and centrifuge rotor 301 becomes ready to accept the subsequent sample racks.

Some of the sample racks 10 withdrawn to partitive line unit 1c and designated to stop over at cap-opener unit 4 are stopped once on partitive line unit 1c to be retained temporarily in buffer unit 2b when there exists a preceding sample rack on a partitive line unit 1d which is coupled in a pair with cap-opener unit 4, or when the cap-opener unit 4 is full of preceding sample racks. The retained sample racks are kept waiting in buffer unit 2b until partitive line unit 1d and cap-opener unit 4 become ready to accept the following sample racks. If no preceding sample rack exists on partitive unit line 1d and cap-opener unit 4 becomes ready to accept the following sample racks, the subsequent sample racks kept waiting in buffer unit 2b are allowed to move to cap-opener unit 4 via partitive line units 1c and 1d. There are cases where the sample rack moved to partitive line unit 1c is delivered to the cap-opener 4 without being retained in buffer unit 2b. Also in such cases, the sample rack is stopped once on partitive line unit 1d from which it is withdrawn into cap-opener 4 by means of a rack transfer mechanism such as robot hands. Other sample racks which do not need to be withdrawn into the cap-opener 4 are allowed to move to a partitive line unit 1e adjoining thereto without stopping on the partitive line unit 1d. The sample rack which accommodates sample containers subjected to cap-opening operation in the cap-opener unit 4 is withdrawn onto partitive line unit 1d.

Some of the sample racks 10 on partitive line unit 1d which is designated to stop over at on-line aliquoter unit 5 is moved to partitive line unit 1e which is coupled with aliquoter unit. 5 if there exists no preceding sample rack on the partitive line unit 1e. Then, it is transferred therefrom into aliquoter unit 5 by the transfer mechanism. Other sample racks which do not need to be subjected to the operation in aliquoter unit 5 are allowed to pass through partitive line unit 1e without being withdrawn into the aliquoter unit.

In the aliquoter unit 5, rack IDs of the mother sample rack 10 and the daughter sample rack are read out respectively by a bar code reader. Sample IDs of the samples on the mother sample rack are already read out by ID information reader 15, and are identified in the central controller 17. Daughter sample rack 19 the rack ID of which has been read is positioned in a pipetting station of aliquoter unit 5, and the mother sample rack 10 transferred from partitive line unit 1e is also position in the pipetting station. A relationship between a sample to be aspirated by the pipetting device in the pipetting station and a container on the daughter sample rack into which the aspirated sample is to be injected is identified by the controller in reference to these two rack IDs as a key.

A particular sample to be subjected to the aliquoter handling, i.e., to aspirate the sample from the mother sample container and inject the aspirated sample into the daughter sample container on the daughter sample rack 19, is designated by the central controller 17. The mother sample rack 10 and the daughter sample rack 19 having been through the aliquoter handling are withdrawn from aliquoter unit 5 to its partitive line unit 1e. The majority of the sample racks 10 supplied from rack loading device 50 are caused to stop over at the on-line aliquoter unit 5.

Of these sample racks 10, 19 withdrawn to partitive line unit 1e, only the daughter rack 19 is caused to stop over at bar code labeler unit 6 in the next stage. The daughter sample rack 19 destined to stop over at the unit 6 is moved from partitive line unit 1e to partitive line unit 1f, then after stopping once thereon, it is withdrawn into unit 6. In the handling unit 6, the rack ID of the daughter rack 19 is read out. Because the relationship between the mother and the daughter is already identified by the controller, bar code labeler unit 6 issues a bar code label which has the same sample ID as the corresponding mother sample ID to each daughter sample container accommodated on daughter sample rack 19, and pastes a corresponding label on the external wall of each daughter sample container. After reading and verification of the pasted bar codes by the bar code reader, the daughter sample rack 19 is discharged from labeler unit 6 to its partitive line unit 1f. Other sample racks 10,19 which do not need to stopover at bar code labeler unit 6 are caused to advance to partitive line unit 1g in the next stage without stopping on partitive line unit 1f.

In the same way, sample rack 10, 19 destined to stop over at restoppler unit 7 is stopped once on partitive line unit 1g, then is withdrawn into restoppler unit 7. The unit 7 seals the sample containers on the withdrawn sample rack with caps, then discharges the sample rack to partitive line unit 1g. Other sample racks 10, 19 which do not need to stop over at restoppler unit 7 are moved toward partitive line unit 1h in the subsequent stage without stopping over at restoppler unit 7.

Further, sample racks 10, 19 destined to stop over at sorting unit 8 are withdrawn into sample sorting unit 8 via partitive line unit 1h associated therewith. Only such test tubes, which serve as the sample containers on the withdrawn sample racks 10 and 19, and are requested are transferred to their designated sorting positions using a robot hand. After completion of the transfer, the sample racks 10, 19 are discharged to partitive line unit 1h. Other sample racks which are not destined to stop over at the sorting unit 8 are allowed to move on bypassing the sorting unit 8.

Still further, sample rack 10, 19 which is designated to stopover at an off-line aliquoter unit or analyzing unit 9 is transported to partitive line unit 1i, and stopped once on that unit 1i, then withdrawn, for example, into analyzing unit 9. The sample rack subjected to a sample collection handling in the pipetting station provided within the analyzing unit is discharged to partitive line unit 1i. The analyzing unit 9 collects only such samples on the sample rack which are requested to be analyzed into reaction vessels provided within analyzing unit 9. The sample rack handed over from the analyzing unit to partitive line unit 1i is then transported to rack storage device 60. Those sample racks which have been transported to partitive line unit 1h and do not need to stopover at analyzing unit 9 are also transported to the rack storage device 60 via partitive line unit 1i.

Any sample rack the handling operation of which by a particular handling unit in the system is reset, or there occurred errors involved in handling operations by the centrifuge, cap-opener, aliquoter and the like, is withdrawn into a default buffer area 14 within rack storage device 60. Such sample racks are transferred from default buffer area 14 to a priority sample mounting area 13, and are returned to rack loading device 50 via a feedback transportation line of the transportation line 1, then the same is again supplied from emergent sample mounting position 12 to the main transportation line.

FIG. 2 shows a status of the sample handling system of the invention in which buffer units 2a, 2b and all of the handling units 3–9 are removed from the transportation line 1. A core structural portion of the handling system which includes transportation line 1, rack loading device 50 and rack storage device 60 is not disassembled during normal maintenance work. The core structural portion communicates information on the transportation operation of each sample rack directly with the central controller 17. On the other hand, the buffer units 2a, 2b and the handling units 3–9 communicate information on the operation of their own units indirectly with the central controller 17 via the core structural portion. Accordingly, the sample rack is allowed to be transported entirely by the core structural portion alone. Although the status in which all of the handling units 3–9 are removed is shown in FIG. 2, in the same manner, the sample rack can be transported entirely by the transportation line 1 even in such a status where only one or two units thereof are removed. That is, even after any of the plural handling units 3–9 is removed. from its partitive line unit 1a–1i provided corresponding thereto in a pair, the sample rack can be transported on its partitive line unit which is devoid of the corresponding handling unit provided as a pair.

A longitudinal dimension of partitive line unit 1b in the direction of transportation of the sample rack is substantially the same as a width of centrifuge unit 3 disposed in a pair therewith. Longitudinal dimensions of other partitive line units 1d–1i relative to widths of their handling units 4–9 corresponding thereto are the same as above. Therefore, a gap between any two adjacent handling units can be made in a close proximity from each other, thereby eliminating redundant spacing in the transportation line 1 which is comprised of a combination of plural partitive line units connected in series. As a result, the entire size of the system can be made compact.

As shown in FIG. 2, the plural handling units which are disposed as per thes system configuration, can be removed individually from their partitive line units in the direction of arrows 40. In a condition where a particular handling unit is removed, the sample rack cannot stopover at the removed particular handling unit, but can pass through its partitive line unit which makes a pair with the removed handling unit. In addition, dotted lines with arrows in the drawing show the routes of movement (transportation) of the sample racks in the system when the handling units therein provided in pairs are coupled with their partitive line units.

With reference to FIG. 3, modes of information communication between respective handling units and the central controller of FIG. 1 will be described. The core structural portions such as rack loading device 50, rack storage device 60 and transportation line 1 are connected via communication cables 53a–53j. The rack loading device 50 which supervises the core structural portions is connected with central controller 17 via communication cable 52. Each buffer unit 2a, 2b and each handling unit 3–9 are connected to each corresponding partitive line unit 1a–1i forming a pair therewith via communication cables 71–79. Therefore, operational information on the transportation of sample racks by each handling unit is transmitted to the central controller via each partitive line unit provided in a pair therewith.

Information on operational conditions which is not related to the transportation of the sample racks is communicated between specified handling units and central controller 17 via communication cables 81–84.

Each of the plural partitive line units carries out communications with neighboring partitive line units, with its corresponding handling unit in a pair therewith, and with the central controller 17, respectively. Through these communications, stop-over of the sample rack at a particular handling unit is executed upon confirmation by the central controller 17 that the particular handling unit is ready to accept the subsequent sample rack, and under control of the transportation line 1 by the central controller 1. The on-line aliquoter unit 5 and off-line aliquoter unit 9 communicate information on their aliquoting operation with the central controller 17. Bar code labeler unit 6 communicates labeling information with the central controller 17. Further, sample sorting unit 8 communicates sorting information with the central controller, and analyzing unit 9 communicates aliquoting and analysis information with the central controller, respectively.

Figure 4:
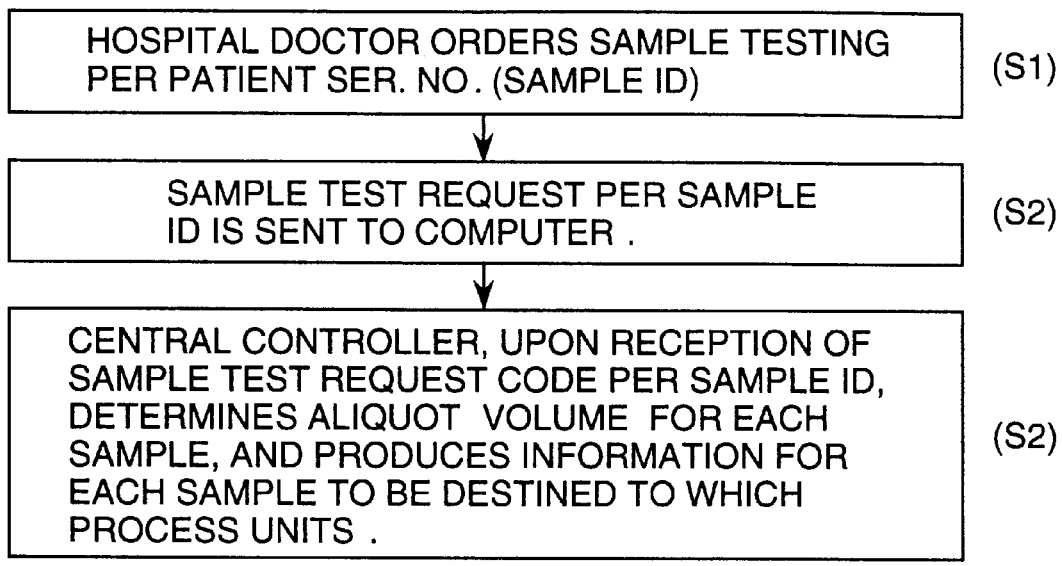
FIG. 4 is a flow chart indicating steps for requesting sample testing to the sample handling system through a host computer in a clinic laboratory.

Now, with reference to FIGS. 4, 5 and 6, operations of the sample handling system of FIG. 1 will be described. FIG. 4 depicts a flow for requesting sample tests to the sample handling system through a host computer of a clinic laboratory. A doctor at a hospital requests what analysis items to be analyzed for each sample (step 1). Then, contents of the request, sample IDs and analysis items which are coded are transmitted to the laboratory computer (step 2). These coded request information is transmitted from the laboratory computer to central controller 17, wherein a pipetting quantity for each sample is determined, and a stopover information for each sample to stop over at which handling unit is generated (step 3).

Figure 5:
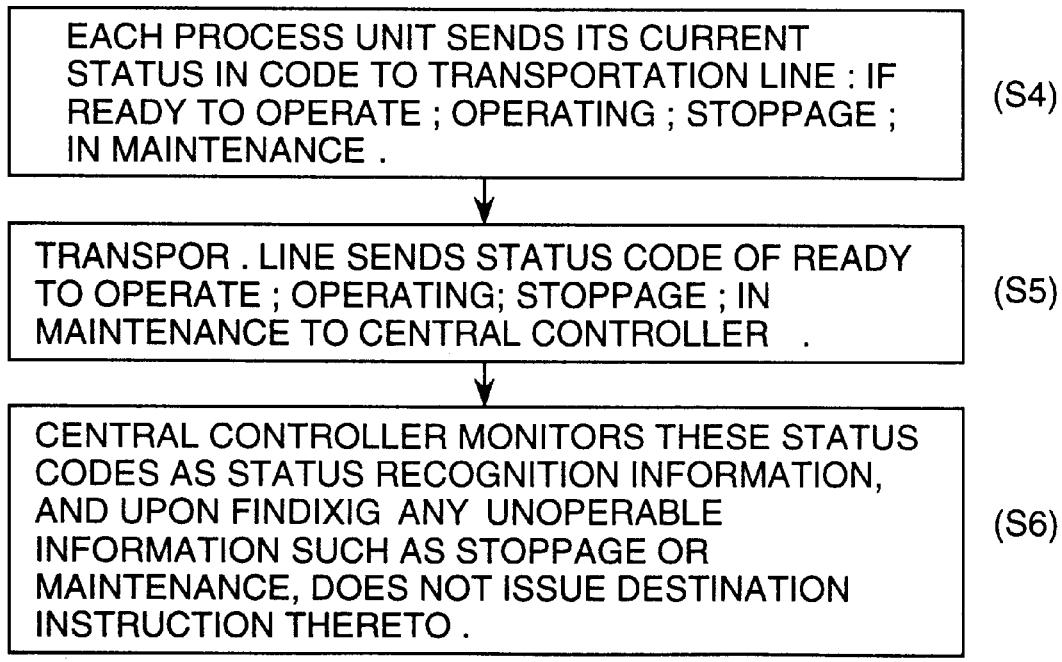
FIG. 5 is a flow chart indicating steps for transmitting the operational status of each handling unit in the sample handling system of FIG. 1.

FIG. 5 shows a flow of steps for transmitting information on the operational status regarding the transportation of the sample rack by each handling unit according to the embodiment of FIG. 1. Respective buffer units 2a, 2b and handling units 3–9 which constantly keep in communication with their counterparts of the partitive line units, transmit coded information on their own statuses indicative of if they are "ready to operate", "under operation", "at stoppage" or "under maintenance" (step 4). The transportation line 1 which is constantly in communication with central controller 17 transmits a status code received from each unit to the central controller (step 5). The central controller 17 monitors these status codes as ID information, and if there occurs any inoperative status code (such as "at stoppage" or "under maintenance"), the same will not issue a stopover instruction for the sample rack to stop over at that handling unit which is the sender of that inoperative information (step 6).

Figure 6:
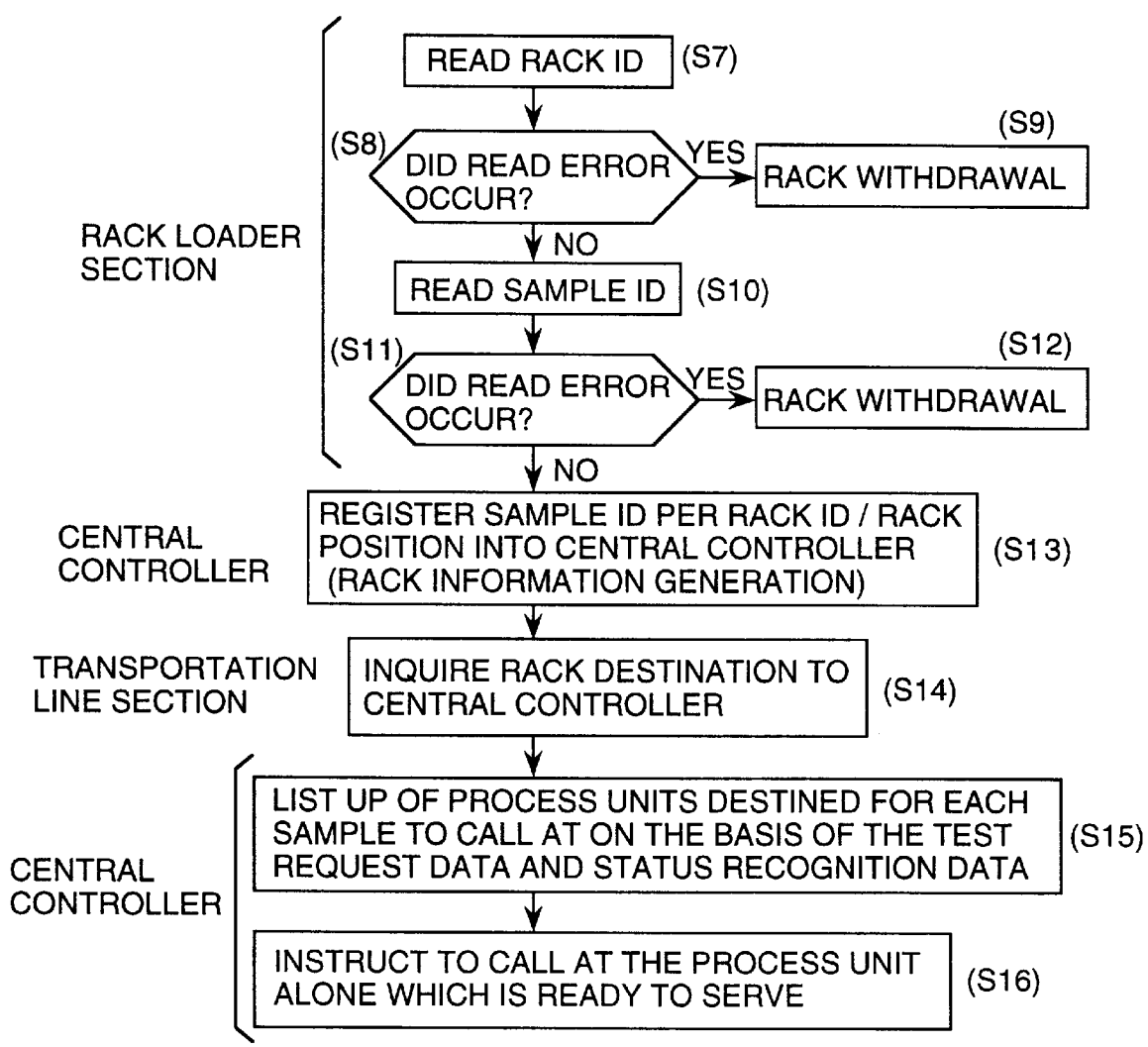
FIG. 6 is a control flow chart indicating steps for controlling the transportation of each sample rack to which handling unit the same should be delivered.

FIG. 6 shows a stopover control flow for the sample rack. In the rack loading device 50, information reader 15 reads out rack. ID information (step 7) and sample ID information per rack position (step 10) to be registered in the central controller 17 (step 13). In steps S8 and S11, it is judged if there occurred any read errors, and such sample racks in which error occurred are withdrawn into rack withdrawing area 16 (S9, S12). On the basis of the rack IDs and sample IDs having been read out, the central controller 17 generates and stores a table which correlates respective sample IDs for respective samples as per respective rack positions on each sample rack. The transportation line 1 makes inquiry about stopover allowance for each sample rack to the central controller 17 (Step 14). In response to this inquiry, the central controller 17 lists up the handling units at which the sample rack should stop over on the basis of the stopover information generated in step 3 and the status monitoring information obtained in step 6 (step 15: S15). The central controller 17 instructs the transportation line 1 to allow for the sample rack to stopover only at the designated handling units listed as available on the list (step 16: S16). Then, the transportation line 1 controls the transport of the sample rack to stopover only at the designated handling units.

As described hereinabove, in the sample handling system of the invention, the central controller 17 keeps monitoring of operation of each one of the plural handling units in the system to verify that the sample rack is allowable to be handled by which handling unit, then selectively determines for the sample rack at which handling units it should stop over on the basis of the status monitoring information on each handling unit and ID information read out by the ID information reader. In addition, the central controller 17 provides the determined stopover information to the transportation line.

Further, in the embodiment of the invention, each one of the plural handling units which constitute the system issues an inoperative information when it becomes inoperative to the transportation line. In response to this inoperative information from the handling unit which is inoperable or will become inoperable due to scheduled maintenance work, the transportation line transmits this inoperable or scheduled inoperable information to the central controller. The central controller or the transportation line controller controls the transport operation of the sample racks on the transportation line such that the sample racks do not stopover at the particular handling unit which is defined inoperative.

Still further, in the sample handling system according to the invention, the sample rack designated to stopover at a particular handling unit among the plural handling units disposed within the system is allowed to be withdrawn into this designated particular handling unit through its partitive line unit only when there exists no preceding sample rack on the partitive line unit which is coupled to the designated particular handling unit as a pair.

Figure 7:
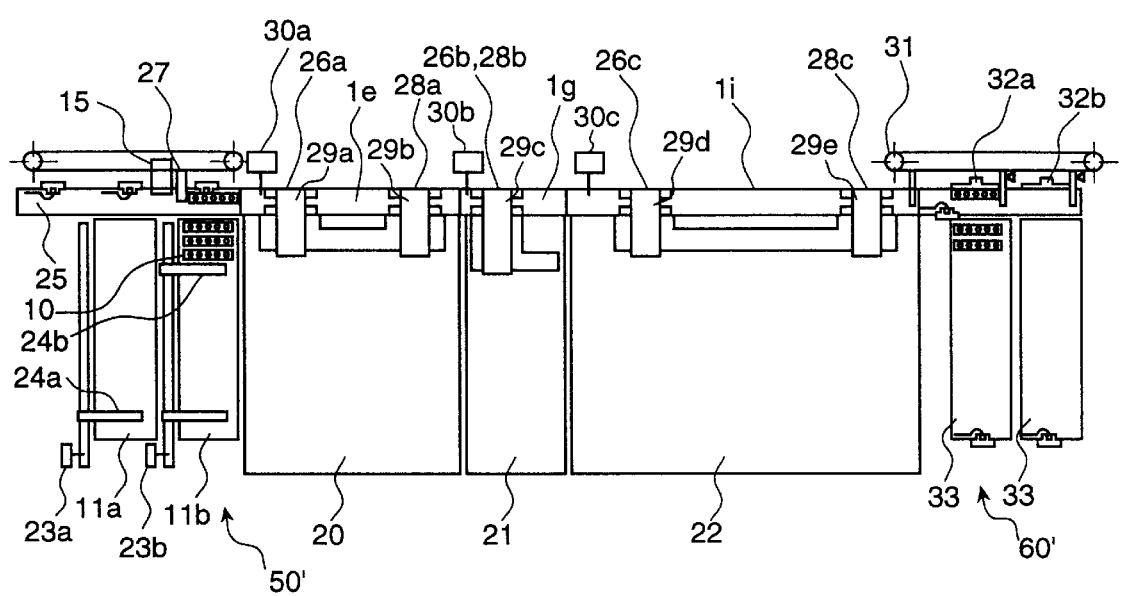
FIG. 7 is a schematic block diagram indicating another embodiment of the invention, and another arrangement of a plurality of handling units.

FIG. 7 is a schematic block diagram indicating another arrangement of handling units in a sample handling system of another embodiment according to the invention. This another embodiment which is provided with three different handling units is wholly for explaining a sample rack transport mechanism of the invention. This operation is as follows. When the system starts its operation after sample racks 10 are installed in normal sample rack loading area 11a, 11b in a rack loading device 50', feed lever motor 23a, 23b is energized to drive feed lever 24a, 24b so as to transport sample rack 10 toward feeder line 25 serving also as the code reader line. On the feeder line 25, its transport motor is started to move sample rack 10 toward the transportation line using a feeder tooth 27. The sample rack 10, after having its rack code number and sample ID numbers of the samples thereon read by reader 15, is transported to a partitive line unit 1e. The sample rack 10 is allowed to be withdrawn into respective handling units 20, 21 and 21 from the transportation line 1 which is comprised of respective partitive line units 1e, 1g and 1i, through their respective inlet ports 26a, 26b and 26c, by operation of their respective transfer mechanisms 29a, 29c and 29d. Then, by operation of their respective transfer mechanisms 29b, 29c and 29e, the sample rack 10 is discharged therefrom through their exit ports 28a, 28b and 28c. Respective partitive line units 1e, 1g and 1i are provided with respective belt conveyers which are driven by transport motors 30a, 30b and 30c corresponding thereto.

As for the inlet ports and outlet ports, the handling units 20 and 22 have their inlet and outlet ports at different positions, while the handling unit 21 has its inlet and outlet ports at the same common position. The sample rack 10 discharged on the transportation line is transported to rack storage device 60' driven by operation of transport motor 31 therein, then is pushed by operation of thrust mechanism 32a, 32b to be stored in rack storage area 33.

The embodiment of FIG. 7 also has the same arrangement as the another embodiment of FIG. 1 at least with respect to the rack transfer mechanisms provided between the transportation line and each handling unit. Further, with respect to the control of the rack transportation in the embodiment of FIG. 7, it is the same as in the case of FIG. 1. By way of example, in FIG. 7, handling unit 20 depicts an aliquoter unit, handling unit 21 depicts a cap-opener unit, handling unit 21 depicts a restopper unit, and handling unit 22 depicts an analyzing unit.

According to the embodiments of the invention as described with reference to FIGS. 1 and 7, even in such a case where any part of the plural handling units within the system is in an inoperative state, i.e., unable to handle the sample rack, the sample handling is ensured to be executed by the remaining handling units in the system. Further, according to the embodiments of the invention, the sample rack which carries plural samples thereon can be moved in such a manner to stopover at the designated handling unit by which some of the samples need to be treated, and to pass by without stopping at the other handling unit by which the samples need not be treated. Still further, when the designated handling unit by which the samples need to be treated is stopped due to failure or is inoperative during maintenance work, the sample rack is allowed to advance to the next handling process without stopping over at that inoperative handling unit. Furthermore, because the transportation line of the system includes plural transportation line units which are provided in pairs with respective handling units corresponding thereto, and the respective handling units can be removed from their corresponding transportation line units, a pattern of combination for the system configuration can be defined by each pair of the partitive line unit and its associated handling unit. Therefore, any such large scale improvements in the hardware as well as in the software that require a total reconfiguration of the system can be avoided, thereby reducing enormous time and cost needed in such improvements.

What is claimed is:

1. A sample handling system including: a transportation line for transporting a sample rack which holds samples; a rack loading device for supplying said sample rack to said transportation line; a rack storage device for storing said sample rack transported by said transportation line; and a plurality of handling units disposed along said transportation line for applying a treatment on the samples held on said sample rack, or on containers containing said samples, said sample handling system further comprising:

an identification (ID) information reader for reading an ID information of a sample rack to be transported;

a central controller which monitors operational status of each handling unit and determines for each sample rack at which handling unit to stopover on the basis of the read-out ID information thereof, a centrifuge unit and an aliquoter unit provided as part of said plurality of handling units;

a partitive line unit for said centrifuge unit and a partitive line unit for said aliquoter unit each being a part of said transportation line; and unit controllers contained in said partitive line units, respectively, each of said unit controllers controlling operation of a respective partitive line unit and mediating information between a related handling unit and said central controller.

2. A sample handling system according to claim 1, wherein:

said transportation line comprises a plurality of partitive line units connected in series, each of said plurality of partitive line units being provided in a pair with each of said plurality of handling units, respectively; and even after any of said plurality of handling units is removed from the corresponding partitive line unit provided in the pair therewith, said sample rack is ensured to be transported on the partitive line unit without the corresponding handling unit.

3. A sample handling system according to claim 2, wherein the sample rack designated to stop over at one handling unit among the plural handling units of the system is allowed to be delivered into said one handling unit through a partitive line unit corresponding thereto only when there exists no preceding sample rack on a partitive line unit which is provided as a pair with said particular handling unit.

4. A sample handling system according to claim 1, further comprising a rack withdrawing area for withdrawing a sample rack, which is disposed in the vicinity of a read-out position of said ID information reader, whereby any sample rack which failed to be read out by said ID information reader is withdrawn into said rack withdrawing area so as not to be allowed to stop over at any handling unit.

5. A sample handling system combining a plurality of sample handling units capable of handling samples carried on a sample rack, the plurality of sample handling units being arranged along a transportation line for transporting the sample rack, comprising:

a means for reading identification (ID) information of said sample rack; and a central controller for controlling said transportation line, a centrifuge unit and an aliquoter unit provided as part of said plurality of handling units;

a partitive line unit for said centrifuge unit and a partitive line unit for said aliquoter unit each being a part of said transportation line; and unit controllers contained in said partitive line units, respectively, each of said unit controllers controlling operation of a respective partitive line unit and mediating information between a related handling unit and said central controller, wherein:

said central controller monitors statuses of said plurality of handling units, determines whether or not to allow said sample rack to stop over at each handling unit on the basis of status information obtained by monitoring and read-out said ID information, and transmits thus determined stop-over information to said transportation line; and said transportation line, in response to the transmitted stop-over information, controls the transport of said sample rack.

6. A sample handling system according to claim 5, wherein said transportation line comprises a combination of a plurality of said partitive line units, each forming a pair with each handling unit of the system, and wherein said each handling unit is installed removably from its corresponding partitive line unit provided in a pair therewith.

7. A sample handling system according to claim 6, wherein a length of each of said plurality of partitive line units in the transport direction of said sample rack is substantially the same as a width of each of said plural handling units forming each pair therewith.

8. A sample handling system according to claim 1, which further comprises a buffer unit disposed between said ID information reader and said centrifuge unit.

9. A sample handling system according to claim 8, wherein sample racks of the same number as that capable of being contained in a centrifuge rotor in said centrifuge unit or less are delivered from said partitive unit for said centrifuge unit to said buffer unit.

* * * * *